(12) United States Patent
Lemer

(10) Patent No.: US 12,300,398 B2
(45) Date of Patent: May 13, 2025

(54) ANTI-RADIATION VIEWING PORT

(71) Applicant: LEMER PAX, La Chapelle sur Erdre (FR)

(72) Inventor: Pierre-Marie Lemer, Nantes (FR)

(73) Assignee: LEMER PAX, La Chapelle-sur-Erdre (FR)

( * ) Notice: Subject to any disclaimer, the term of this patent is extended or adjusted under 35 U.S.C. 154(b) by 325 days.

(21) Appl. No.: 18/014,459

(22) PCT Filed: Jul. 5, 2021

(86) PCT No.: PCT/EP2021/068544
§ 371 (c)(1),
(2) Date: Jan. 4, 2023

(87) PCT Pub. No.: WO2022/008461
PCT Pub. Date: Jan. 13, 2022

(65) Prior Publication Data
US 2023/0335306 A1    Oct. 19, 2023

(30) Foreign Application Priority Data
Jul. 6, 2020   (FR) ........................................ 2007147

(51) Int. Cl.
*G21F 1/06*       (2006.01)
*A61B 6/10*       (2006.01)
(Continued)

(52) U.S. Cl.
CPC ................ *G21F 1/06* (2013.01); *A61B 6/107* (2013.01); *G21F 1/125* (2013.01); *G21F 3/00* (2013.01)

(58) Field of Classification Search
CPC .... G21F 1/06; G21F 3/00; F21F 1/125; A61B 6/107
See application file for complete search history.

(56) References Cited

U.S. PATENT DOCUMENTS

2010/0164492 A1\* 7/2010 Leussler .............. G01R 33/422
324/307
2018/0325473 A1   11/2018 Valade et al.
(Continued)

FOREIGN PATENT DOCUMENTS

CN          209874971         12/2019
DE     10 2008 009 776       10/2009
(Continued)

OTHER PUBLICATIONS

International Search Report for PCT/EP2021/068544 dated Sep. 29, 2021, 4 pages.
(Continued)

*Primary Examiner* — Nicole M Ippolito
(74) *Attorney, Agent, or Firm* — NIXON & VANDERHYE

(57) ABSTRACT

Disclosed is an anti-radiation viewing port intended to be fitted to a wall opening provided in a wall which separates a space subjected to ionising radiation, the space being called a hot space, and a space which is not subjected to ionising radiation, the space being called a cold space. This anti-radiation viewing port includes a screen which is made from transparent radio-protective material and which is associated with a peripheral attachment frame. A joint structure is positioned between a rebate periphery wing of the peripheral attachment frame, and a peripheral screen edge; and the front screen face of the screen made of transparent radio-protective material, the front joint face of the joint structure and at least a portion of the outer face of an attachment wing which extends in continuation of the front joint face are located in the same plane or substantially in the same plane.

20 Claims, 2 Drawing Sheets

(51) Int. Cl.
*G21F 1/12* (2006.01)
*G21F 3/00* (2006.01)

(56) References Cited

U.S. PATENT DOCUMENTS

2020/0100736 A1\* 4/2020 Lemer ..................... G21F 3/00
2020/0276886 A1\* 9/2020 Tosetto ................. B60J 1/2094

FOREIGN PATENT DOCUMENTS

EP          0 241 665      10/1987
WO        2017/077259       5/2017

OTHER PUBLICATIONS

Written Opinion of the ISA for PCT/EP2021/068544 dated Sep. 29, 2021, 7 pages.

\* cited by examiner

ANTI-RADIATION VIEWING PORT

CROSS-REFERENCES TO RELATED APPLICATIONS

This application is the U.S. national phase of International Application No. PCT/EP2021/068544 filed Jul. 5, 2021 which designated the U.S. and claims priority to FR2007147 filed Jul. 6, 2020, the entire contents of each of which are hereby incorporated by reference.

BACKGROUND OF THE INVENTION

Field of the Invention

The present invention relates to the technical field of protection against ionising radiation. More particularly, it relates to an anti-radiation viewing port which is intended to be attached to the periphery of an opening provided in a wall which separates a space subjected to ionising radiation (called a hot space), and a space which is not subjected to ionising radiation (called a cold space).

Description of the Related Art

Some hospital or clinic departments have one or more interventional radiology rooms within which surgical procedures are performed under ionising radiation, in particular under X-rays.

Such radiology rooms are surrounded with walls whose inner surface is smooth, to allow for the efficient and simple biological disinfection thereof.

These walls are also adapted to ensure efficient protection against ionising radiation (in particular, X-rays), and they often comprise at least one window, also called "viewing port", providing visual access, from the outside, to the operations carried out inside.

These anti-radiation viewing ports are fitted to a wall opening provided in a wall which separates the hot space and the cold space; and they comprise a screen made of a transparent radio-protective material, associated with a peripheral frame for its attachment to the periphery of the wall opening.

However, the current viewing ports often comprise different rebates, ribs or grooves on the hot space side, which strongly complicate their cleaning and their disinfection.

BACKGROUND OF THE INVENTION

In order to remedy the above-mentioned drawback of the state of the art, the present invention proposes an anti-radiation viewing port intended to be fitted to a wall opening provided in a wall which separates a space subjected to ionising radiation, called a hot space, and a space which is not subjected to ionising radiation, called a cold space, said wall opening being delimited by a front wall face directed towards said hot space, a rear wall face directed towards said cold space and an opening edge connecting said front wall face and said rear wall face, said anti-radiation viewing port comprising a screen made of a transparent radio-protective material, delimited by a rear screen face intended to be directed towards said cold space, a front screen face intended to be directed towards said hot space, and a peripheral screen edge, said screen made of a transparent radio-protective material is associated with a peripheral attachment frame for its attachment to the periphery of said wall opening, characterized in that said peripheral attachment frame comprises:

a rebate bearing wing against which the periphery of said rear screen face is intended to bear, a rebate periphery wing, opposite which the peripheral screen edge is intended to be positioned, a distance being provided between said rebate periphery wing and said peripheral screen edge, an attachment wing extending said rebate periphery wing, said attachment wing comprising (a) an inner face intended to bear against said front wall face, and (b) an opposite outer face, a joint structure being interposed between said rebate periphery wing and said peripheral screen edge, said joint structure comprising a front joint face extending between said front screen face and said attachment wing, said front screen face, said front joint face, and at least part of said outer face of the attachment wing which extends in continuation of said front joint face, being located in a same plane or substantially in a same plane.

Such an anti-radiation viewing port design thus comprises a very flat surface on the hot space side, which facilitates its cleaning and its disinfection.

Other non-limiting and advantageous features of the anti-radiation viewing port according to the invention, taken individually or according to all the technically possible combinations, are the following:

the peripheral attachment frame comprises a plurality of profiles made of a non radio-protective material assembled together, said profiles comprising added inserts made of a radio-protective material, suitable to ensure radio-protection continuity between said hot space and said cold space. Preferably, the anti-radiation viewing port thus comprises (a) at least one insert made of a radio-protective material, added into or onto said attachment wing, and (b) at least one insert made of a radio-protective material added into or onto said rebate bearing wing.

Such a structure leads to an optimum compromise between production cost and radio-protection quality.

the peripheral attachment frame comprises four profiles assembled two-by-two at the corners by attachment squares.

the inner face of the attachment wing is assembled by bonding with said front wall face, preferably by means of a dual-side adhesive.

the rear screen face is assembled by bonding with said rebate bearing wing, preferably by means of a dual-side adhesive.

the joint structure consists of a resin, preferably a resin of the epoxy type.

the rebate periphery wing is continued, in its plane and on the opposite side to said attachment wing, by an attachment extension suitable to allow the assembly of said peripheral attachment frame with the opening edge of the wall opening, by means of attachment screws.

Obviously, the different features, alternatives and embodiments of the invention can be associated with each other according to various combinations, insofar as they are not incompatible or exclusive with respect to each other.

BRIEF DESCRIPTION OF THE DRAWINGS

Moreover, various other features of the invention emerge from the appended description made with reference to the drawings that illustrate a non-limiting embodiment of the invention, and wherein.

DESCRIPTION OF THE PREFERRED EMBODIMENTS

Figure 1:
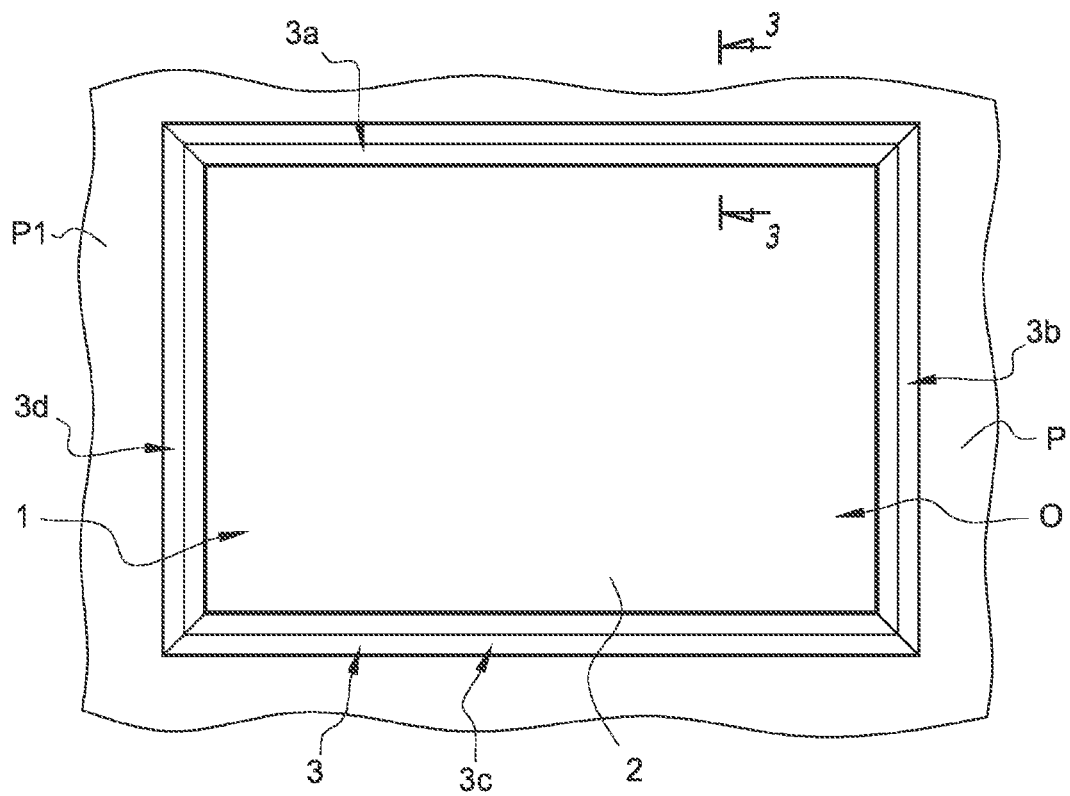
FIG. 1 is a schematic front view of a possible embodiment of an anti-radiation viewing port according to the invention.
Figure 2:
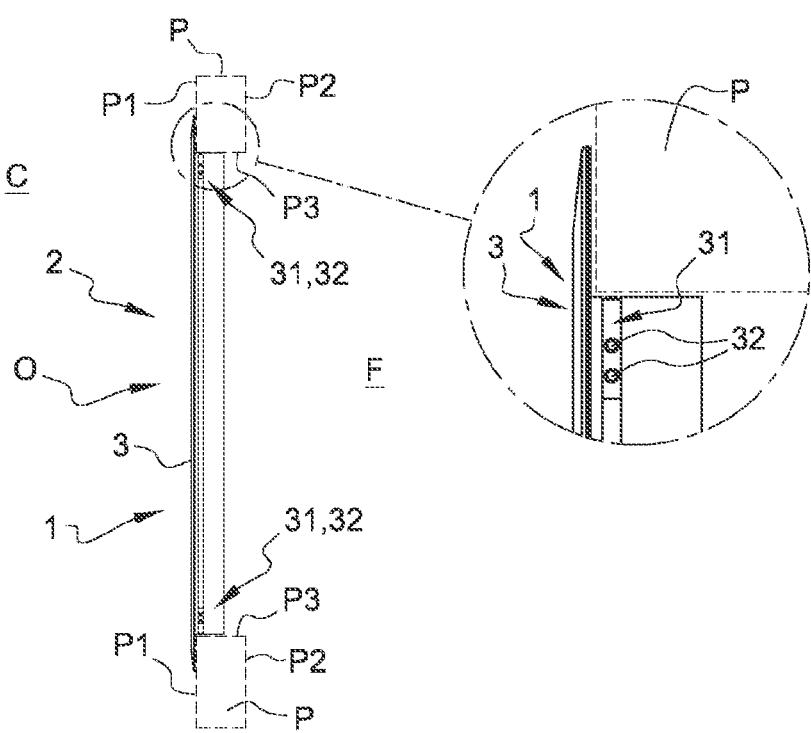
FIG. 2 is a side view of the anti-radiation viewing port illustrated in FIG. 1.
Figure 3:
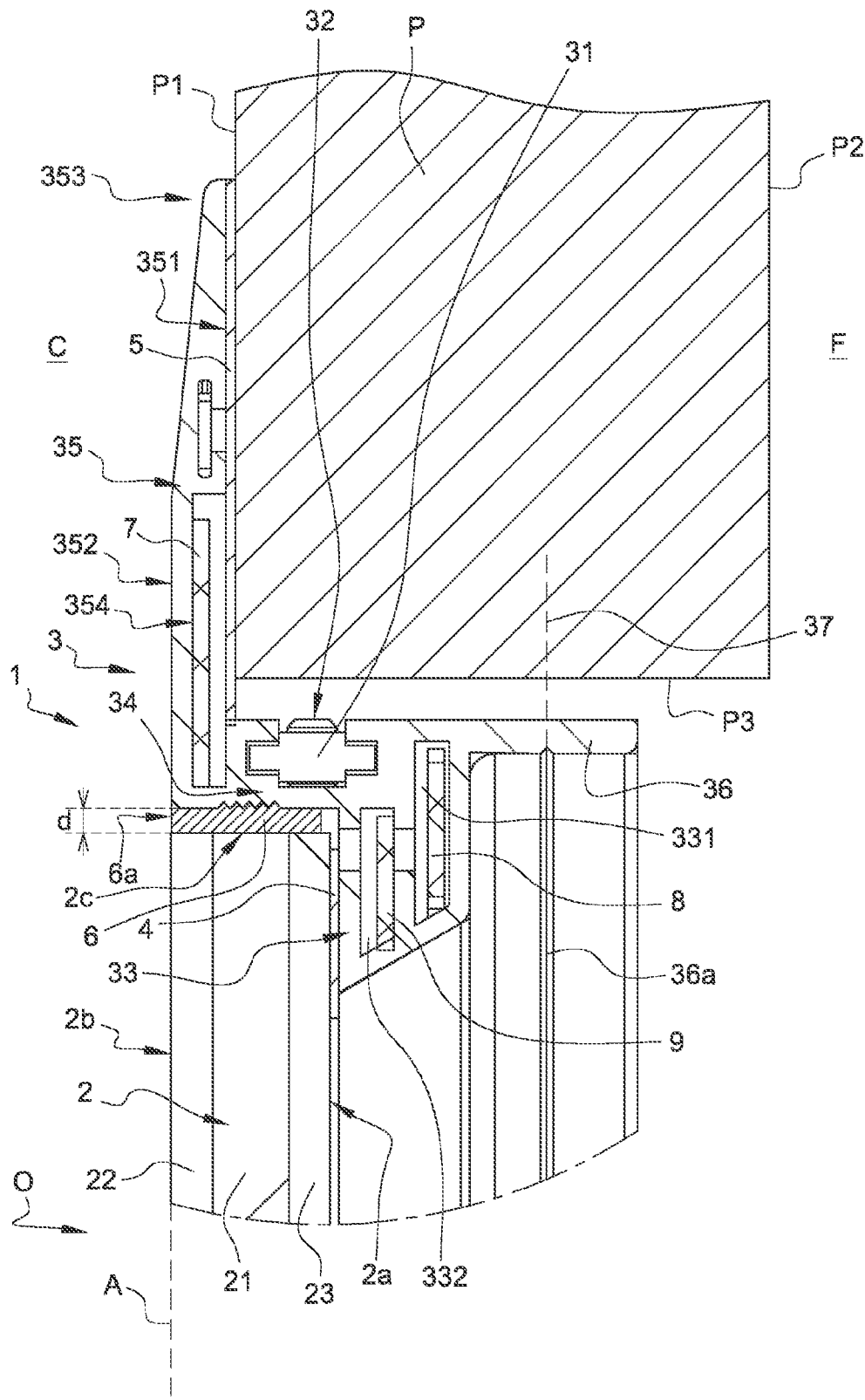
FIG. 3 is a cross-sectional view of the anti-radiation viewing port along the cross-sectional plane 3-3 of FIG. 1.

The anti-radiation viewing port 1 illustrated in FIGS. 1 to 3 is added into a wall opening O provided in a wall P which separates a hot space C (subjected to ionising radiation, for example X-rays) and a cold space F (not subjected to ionising radiation).

The wall P is a wall made of a radio-protective material. It may be made of concrete, and its thickness may be between 100 and 300 mm.

The anti-radiation viewing port 1 is adapted to allow a person located on the cold space F side visual access into the hot space C.

The wall opening O is delimited by a front wall face P1 directed towards the hot space C, a rear wall face P2 directed towards the cold space F and an opening edge P3 connecting the front wall face P1 and the rear wall face P2. Here, the front wall face P1 and the rear wall face P2 extend parallel to each other; and the opening edge P3 extends perpendicular to the front wall face P1 and the rear wall face P2.

The anti-radiation viewing port 1 comprises a screen 2 made of a transparent radio-protective material and a peripheral attachment frame 3 for its attachment to the periphery of the wall opening O.

The peripheral attachment frame 3 is attached to the periphery of the screen 2 made of a transparent radio-protective material.

The screen 2 made of a radio-protective material may be consisted of a central layer 21 made of lead glass, of 6 to 14 mm thick, surrounded by two layers of protective glass 22, 23 of 2 to 4 mm thick. The two layers of protective glass 22, 23 are assembled with the central layer 21 made of lead glass, to form together a single piece.

This screen 2 made of a radio-protective material is delimited by a rear screen face 2*a* intended to be directed towards the cold space F, a front screen face 2*b* intended to be directed towards the hot space C, and a peripheral screen edge 2*c*.

The anti-radiation viewing port 1 here has a generally rectangular shape and the screen 2 made of a radio-protective material has also a generally rectangular shape, just as the peripheral attachment frame 3.

The peripheral attachment frame 3 comprises four profiles 3*a*, 3*b*, 3*c* and 3*d* assembled two-by-two at the corners by attachment squares 31 attached by means of screws 32. The corresponding assembly may be made by means of 45° miter cuts.

Profiles 3*a*, 3*b*, 3*c* and 3*d* have identical cross-sections.

As can be seen in FIG. 3, each profile 3*a*, 3*b*, 3*c* and 3*d* of the peripheral attachment frame 3 comprises, from the inside to the outside: a rebate bearing wing 33, a rebate periphery wing 34 that extends at right angles from the rebate bearing wing 33, and an attachment wing 35 that extends at right angles from the rebate periphery wing 34.

The rebate bearing wing 33 and the rebate periphery wing 34 form together a rebate for receiving a peripheral border of the screen 2 made of a radio-protective material. For that purpose, the peripheral border of the rear screen face 2*a* bears against the rebate bearing wing 33, and the peripheral screen edge 2*c* comes in position opposite the rebate periphery wing 34, by keeping between them a space or a distance d.

The rear screen face 2*a* is attached to the rebate bearing wing 33 (and more particularly, to the face of the rebate bearing wing 33 forming the bearing surface of the rear screen face 2*a*). This attachment is preferably made by bonding and also, preferably, by means of a dual-side adhesive 4.

The attachment wing 35 has an inner face 351 that bears against the front screen face P1, and an opposite outer face 352. The inner face 351 of the attachment wing 35 is attached to the front wall face P1. This attachment is preferably made by bonding and also, preferably, by means of a dual-side adhesive 5.

The outer face 352 of the attachment wing 35 is located in a same plane A (or substantially in the same plane A) as the front screen face 2*b* (at least for the portion of this outer face 352 that is located in the continuation of the front screen face 2*b*).

A joint structure 6 is added to fill the space or the distance d separating the rebate periphery wing 34 and the peripheral screen edge 2*c*. This joint structure 6 comprises a front joint face 6*a* that extends between the front screen face 2*b* and the attachment wing 35, and that is located in the above-mentioned plane A (or substantially in the plane A).

Thus, as can be seen in FIG. 3, the front screen face 2*b*, the front joint face 6*a*, and at least part of the outer face 352 of the attachment wing 35 which extends in continuation of said front joint face 6*a*, are located in the same plane A, or substantially in a same plane A.

That way, on the hot space C side, the anti-radiation viewing port 1 has a flat surface that is very easy to clean and disinfect. The only level difference, or the only height difference, with respect to the plane A is at the periphery of the attachment wing 35 and corresponds to the thickness of the end 353 of this attachment wing 35 (of the order of a few mm).

As can be seen in FIG. 3, the thickness of this attachment wing 35 decreases slightly towards the outside; this for maximally minimizing the end height difference.

The peripheral screen edge 2*c* may have a slight bevel and flare from the front screen face 2*b* towards the rear screen face 2*a* to facilitate the centring during the installation of the screen 2 made of a radio-protective material into its receiving rebate 33, 34. Such a flare makes it possible to obtain a regular distance (distance d) over the whole periphery of the screen 2 made of a radio-15 protective material, between the peripheral screen edge 2*c* and the rebate periphery wing 34. The joint structure 6 is added between the peripheral screen edge 2*c* and the rebate periphery wing 34 to fill the distance d (or the space) between both.

This joint structure 6 is preferably made from a pasty or semi-liquid material having the ability to harden over time, without, or without too much, shrinking. For example, a resin, preferably a resin of the epoxy type, is used.

The profiles 3*a*, 3*b*, 3*c* and 3*d* forming the peripheral attachment frame 3 are preferably made of a non radio-protective material (for example a metal material such as aluminium, a plastic material or also a composite material); and these profiles 3*a*, 3*b*, 3*c* and 3*d* comprise one or several added inserts 7, 8, 9 made of a radio-protective material, suitably structured and positioned to ensure a continuity of radio-protection between the hot space C and the cold space F. In particular, the added inserts 7, 8, 9 made of a radio-protective material are adapted to radio-protect the space located between the opening edge P3 and the peripheral screen edge 2c.

The insert(s) in question may for example be made of tungsten, lead, tantalum, charged compound, or more generally any material capable of attenuating the ionising radiation.

Preferably, these added inserts made of a radio-protective material are fully integrated in the thickness of the profile portions to which they are fitted.

In this case, as can be seen in FIG. 3, an insert 7 made of a radio-protective material is added on the side of the inner face 351 of the attachment wing 35 and arranged in a housing 354 open in said inner face 351 of the attachment wing 35. This insert 7 made of a radio-protective material extends as close as possible to the face of the rebate periphery wing 34 located opposite the joint structure 6.

On the other hand, two inserts 8 and 9 made of a radio-protective material are added in housings, respectively 331 and 332, arranged in the rebate bearing wing 33. The two inserts 8 and 9 made of a radio-protective material are longitudinally offset relative to each other to optimize the radio-protective. The two receiving housings 331 and 332 are open at the two ends of the profiles 3a, 3b, 3c and 3d and the inserts 8 and 9 are positioned thereinto by sliding.

Of course, in alternative embodiments, the number of inserts and their positioning may be different.

According to another alternative embodiment, the profiles 3a, 3b, 3c and 3d forming the peripheral attachment frame 3 may be made of a radio-protective material.

In FIG. 3, it can be observed that the rebate periphery wing 34 can be extended by an attachment extension 36 adapted to allow the assembly of the peripheral attachment frame 3 with the opening edge P3 of the wall opening O. This attachment extension 36 extends in the plane of the rebate periphery wing 34 and on the opposite side to the attachment wing 35. Its assembly with the opening edge P3 of the wall opening O is made by means of attachment screws 37 (one of which is illustrated schematically in dotted lines in FIG. 3).

A longitudinal groove 36a is arranged in the face of the attachment extension 36 that is directed towards the inside of the peripheral attachment frame 3, to facilitate the positioning of the attachment screws 37.

The structure of anti-radiation viewing port according to the invention meets the aseptic and sealing requirements of interventional radiology procedures.

The invention claimed is:

1. An anti-radiation viewing port intended to be fitted to a wall opening provided in a wall which separates a space subjected to ionising radiation, called a hot space, and a space which is not subjected to ionising radiation, called a cold space, said wall opening being delimited by a front wall face directed towards said hot space, by a rear wall face directed towards said cold space and by an opening edge connecting said front wall face and said rear wall face, said radiation viewing port comprising a screen made of a transparent radio-protective material delimited by a rear screen face intended to be directed towards said cold space, a front screen face intended to be directed towards said hot space, and a peripheral screen edge, said screen made of a transparent radio-protective material being associated with a peripheral attachment frame for screen's attachment to the periphery of said wall opening, wherein said peripheral attachment frame comprises:

a rebate bearing wing against which the periphery of said rear screen face is intended to bear, a rebate periphery wing, opposite which the peripheral screen edge is intended to be positioned, a distance being provided between said rebate periphery wing and said peripheral screen edge, an attachment wing extending said rebate periphery wing, said attachment wing comprising an inner face intended to bear against said front wall face, and an opposite outer face, a joint structure being interposed between said rebate periphery wing and said peripheral screen edge, said joint structure comprising a front joint face extending between said front screen face and said attachment wing, said front screen face, said front joint face, and at least part of said outer face of the attachment wing which extends in continuation of said front joint face, being located in a same plane, or substantially in a same plane.

2. The anti-radiation viewing port according to claim 1, wherein said peripheral attachment frame comprises a plurality of profiles made of a non radio-protective material assembled together, said profiles comprising added inserts made of a radio-protective material, suitable to ensure radio-protection continuity between said hot space and said cold space.

3. The anti-radiation viewing port according to claim 2, further comprising at least one insert made of a radio-protective material, added into or onto said attachment wing, and at least one insert made of a radio protective material added into or onto said rebate bearing wing.

4. The anti-radiation viewing port according to claim 3, wherein said peripheral attachment frame comprises four profiles assembled two-by-two at the corners by attachment squares.

5. The anti-radiation viewing port according to claim 3, wherein the inner face of said attachment wing is assembled by bonding with said front wall face.

6. The anti-radiation viewing port according to claim 3, wherein said rear screen face is assembled by bonding with said rebate bearing wing.

7. The anti-radiation viewing port according to claim 2, wherein said peripheral attachment frame comprises four profiles assembled two-by-two at the corners by attachment squares.

8. The anti-radiation viewing port according to claim 2, wherein the inner face of said attachment wing is assembled by bonding with said front wall face.

9. The anti-radiation viewing port according to claim 2, wherein said rear screen face is assembled by bonding with said rebate bearing wing.

10. The anti-radiation viewing port according to claim 1, wherein said peripheral attachment frame comprises four profiles assembled two-by-two at the corners by attachment squares.

11. The anti-radiation viewing port according to claim 10, wherein the inner face of said attachment wing is assembled by bonding with said front wall face.

12. The anti-radiation viewing port according to claim 10, wherein said rear screen face is assembled by bonding with said rebate bearing wing.

13. The anti-radiation viewing port according to claim 1, wherein the inner face of said attachment wing is assembled by bonding with said front wall face.

14. The anti-radiation viewing port according to claim 13, wherein the inner face of said attachment wing is assembled with said front wall face by means of a dual-side adhesive.

15. The anti-radiation viewing port according to claim 13, wherein said rear screen face is assembled by bonding with said rebate bearing wing.

16. The anti-radiation viewing port according to claim 1, wherein said rear screen face is assembled by bonding with said rebate bearing wing.

17. The anti-radiation viewing port according to claim 16, wherein said rear screen face is assembled with said rebate bearing wing by means of a dual-side adhesive.

18. The anti-radiation viewing port according to claim 1, wherein said joint structure consists of a resin, preferably a resin of the epoxy type.

19. The anti-radiation viewing port according to claim 1, wherein said rebate periphery wing is continued, in its said rebate periphery wing's plane and on the opposite side to said attachment wing, by an attachment extension suitable to allow the assembly of said peripheral attachment frame with the opening edge of the wall opening by means of attachment screws.

20. The anti-radiation viewing port according to claim 1, wherein said joint structure consists of an epoxy resin.

\* \* \* \* \*